(12) United States Patent
Migdal

(10) Patent No.: US 8,899,748 B1
(45) Date of Patent: Dec. 2, 2014

(54) AUTOMATED DETECTION OF EYE NYSTAGMUS

(75) Inventor: Brandon Louis Migdal, Rochester, NY (US)

(73) Assignee: Exelis Inc., McLean, VA (US)

( * ) Notice: Subject to any disclaimer, the term of this patent is extended or adjusted under 35 U.S.C. 154(b) by 204 days.

(21) Appl. No.: 13/313,040

(22) Filed: Dec. 7, 2011

(51) Int. Cl.
*A61B 3/14* (2006.01)

(52) U.S. Cl.
CPC ........................................ *A61B 3/14* (2013.01)
USPC .......................................... 351/206; 351/210

(58) Field of Classification Search
USPC .................................................. 351/206, 210
See application file for complete search history.

(56) References Cited

U.S. PATENT DOCUMENTS

| | | | |
|---|---|---|---|
| 7,357,507 B2 | 4/2008 | Waldorf et al. | |
| 2013/0057829 A1* | 3/2013 | Harris et al. | 351/210 |
| 2013/0114043 A1* | 5/2013 | Balan et al. | 351/210 |

OTHER PUBLICATIONS

Karpenko, et al., "Digital Video Stabilization and Rolling Shutter Correction using Gyroscopes", Stanford Tech Report CTSR 2011-03, (7 pages).

* cited by examiner

*Primary Examiner* — Mahidere Sahle
(74) *Attorney, Agent, or Firm* — Edell, Shapiro & Finnan, LLC

(57) ABSTRACT

A system for detection of eye nystagmus in a test subject includes a camera to capture digital images in a series of sequential digital image frames of the test subject's face when the camera is located a selected distance from the test subject, and an analyzer. The analyzer includes a memory configured to store data, and a processor. The processor is configured with logic to detect and track eye movements of the test subject based upon an analysis of digital image frames captured by the camera, where eye movements are tracked via analysis of a plurality of the captured digital image frames on a sequential frame-by-frame basis. The processor is further configured with logic to provide an indication regarding whether the test subject exhibits nystagmus based upon the eye movement detection and tracking.

18 Claims, 7 Drawing Sheets

AUTOMATED DETECTION OF EYE NYSTAGMUS

BACKGROUND

Nystagmus is a rapid involuntary oscillation of the eyeballs. Horizontal Gaze Nystagmus (HGN) refers to the lateral jerking of the eyes as they gaze to the side (e.g., a sudden jerking movement of the eyes in an opposing direction in relation to the direction at which the eyes are gazing). Vertical Gaze Nystagmus (VGN) refers to the vertical jerking of the eyes as they gaze vertically. HGN has been shown to be an effective indicator of alcohol impairment when administered by a trained law enforcement professional during field sobriety testing. HGN and/or VGN testing is administered because, when intoxicated, the brain experiences difficulty correctly controlling the eye muscles which presents as the nystagmus.

It has been demonstrated scientifically that there is a correlation between a Blood Alcohol Concentration (BAC) greater than a certain value (e.g., a BAC>0.10) and the presentation of HGN in an individual. HGN/VGN testing is used to assess the presence of "clues" in the visual tracking of a stimuli that point to intoxication in the test subject. Testing is typically conducted by a trained law enforcement professional by moving a stimuli (e.g., a pen or pen light) through the subject's field of view a number of times while looking for particular "clues" which present as a nystagmus. The professional is required to make a number of subjective determinations of the presence of nystagmus and point at which this nystagmus presents itself. Presentation of nystagmus during portions of the test at specific intervals and prior to a set point relative to geometry of the subject will indicate a failure of the test (e.g., BAC≥0.08), while no presented nystagmus will indicate a pass of the test (e.g., BAC<0.08).

Although the scientific nature, accuracy and reliability of HGN/VGN testing has long been established, there are several issues that affect the admissibility of the testing and results in a legal proceeding. The subjective nature of testing and pass/fail criteria is based upon the observations of a trained law enforcement professional rather than calibrated and tested equipment. A number of jurisdictions in the U.S. provide for the admission as evidence in a legal proceeding the testimony of a conducting law enforcement officer who has training and experience in conducting HGN/VGN and recognizing the characteristics of an intoxicated test subject. However, defense attorneys also often have an understanding of field sobriety testing such that, during a cross examination of the field test officer testifying as to the determination of an intoxicated defendant utilizing HGN/VGN testing, it might be possible to establish inconsistencies in how the test was administered or establish some level of doubt as to how the test results were interpreted by the field test officer. Further, due to the technical nature of the relationship between HGN/VGN testing and intoxication, some jurisdictions may further require expert witness testimony in relation to the testimony by a field officer who performed an HGN/VGN test to establish sobriety of the defendant.

SUMMARY

In accordance with an example embodiment of the present invention, a system for detection of eye nystagmus in a test subject comprises a camera to capture digital images in a series of sequential digital image frames of the test subject's face when the camera is located a selected distance from the test subject, and an analyzer. The analyzer comprises a memory configured to store data, and a processor. The processor is configured with logic to detect and track eye movements of the test subject based upon an analysis of digital image frames captured by the camera, where eye movements are tracked via analysis of a plurality of the captured digital image frames on a sequential frame-by-frame basis. The processor is further configured with logic to provide an indication regarding whether the test subject exhibits nystagmus based upon the eye movement detection and tracking.

In accordance with another example embodiment of the invention, a computer-implemented method for detection of eye nystagmus in a test subject comprises capturing digital images in a series of sequential digital image frames of the test subject's face during a test session in which an administrator moves a stylus toward one side and another side of the test subject's face while instructing the test subject to gaze at the moving stylus. The method further comprises detecting and tracking eye movements of the test subject based upon an analysis of the captured digital image frames, where eye movements are tracked via analysis of a plurality of the captured digital image frames on a sequential frame-by-frame basis, and providing an indication regarding whether the test subject exhibits nystagmus based upon the eye movement detection and tracking.

The above and still further features and advantages of the present invention will become apparent upon consideration of the following detailed description of a specific embodiment thereof, particularly when taken in conjunction with the accompanying drawings wherein like reference numerals in the various figures are utilized to designate like components.

DETAILED DESCRIPTION

A system suitable for use in field testing and automatic determination of a degree of eye nystagmus is designed to be portable and hand-held to facilitate ease of operability in a number of different environments. The system is non-intrusive, requiring little or no contact with the test subject during operation. The automated determination of HGN/VGN responses by test subjects during operation of the device provides a number of benefits, including providing an objective standard as well as recorded data in determining field sobriety in contrast to current tests administered by law enforcement agencies (e.g., a subjective determination by a law enforcement officer, where sobriety is based upon an officer's observation of eye movement by the subject during the test).

Figure 1:
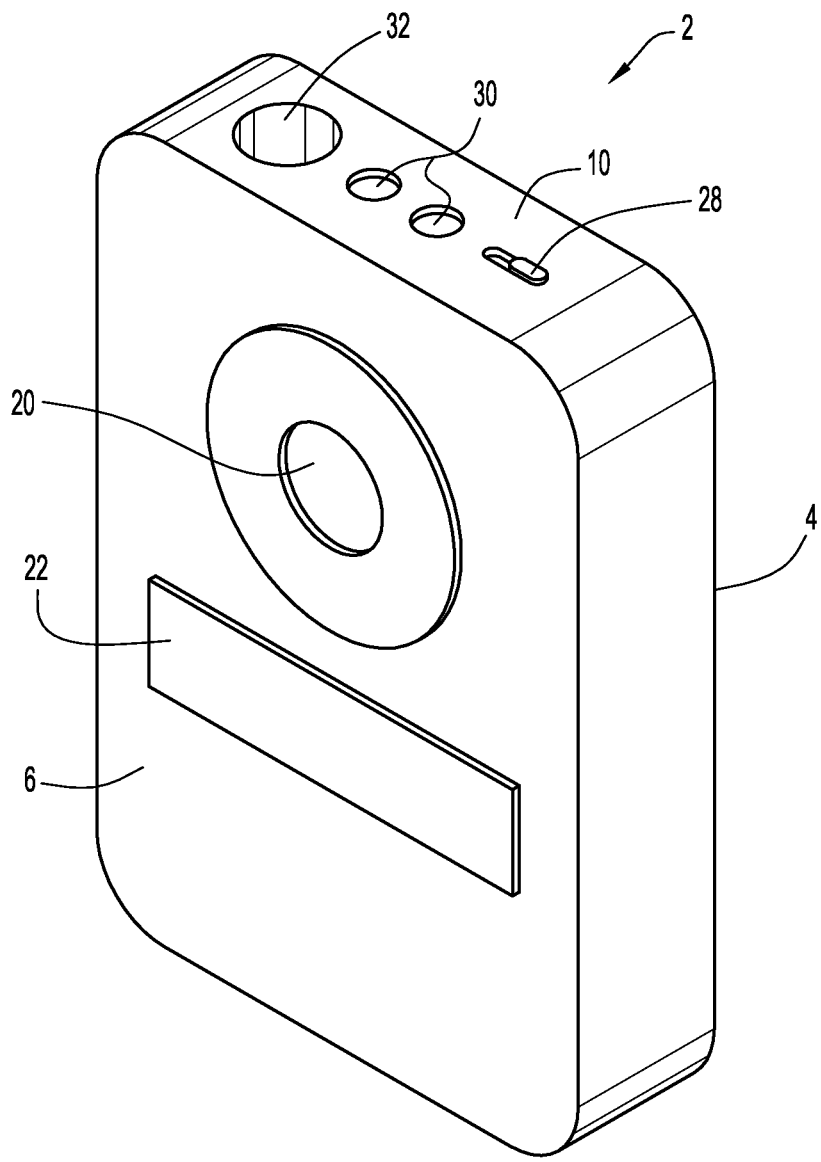
FIG. 1 is a front view in perspective of a nystagmus testing system in accordance with an example embodiment of the invention.
Figure 2:
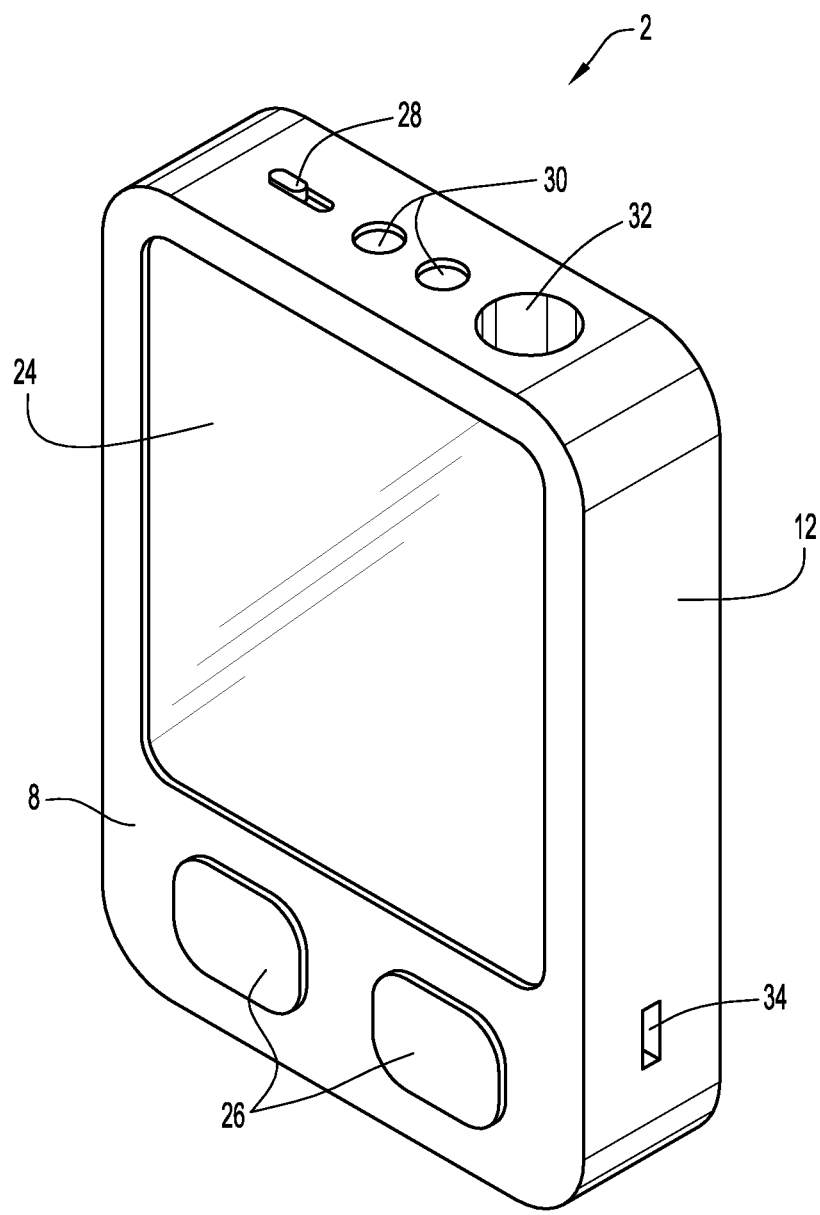
FIG. 2 is a rear view in perspective of the nystagmus testing system of FIG. 1.

An example embodiment of the system is depicted in FIGS. 1-4. Referring to FIGS. 1 and 2, an automated nystagmus testing system 2 comprises a portable, hand-held device 4. The hand-held device 4 is generally rectangular in shape and includes a housing with a front side 6, an opposing rear side 8, and edge portions including an upper edge portion 10 and a side edge portion 12. Each of the front side 6, rear side 8, upper edge portion 10 and side edge portion 12 includes components that facilitate operability of the system 2. The housing can be constructed of any suitably rugged, durable and preferably lightweight materials (e.g., conventional and/or other suitable metal and/or plastic materials used for hand-held or other electronic devices). The device 4 can be of any suitable size that preferably facilitates ease of hand-held use during system operation. For example, the device 4 can have a size on the order of a conventional hand held cellular phone or PDA (personal digital assistant) device (e.g., the device 4 can have a size of about 7-8 cm in width and about 10-11 cm in length).

A digital camera 20 is provided within the housing that is in alignment with a camera aperture disposed on the front side 6 of the device 4. A suitably transparent protective screen (e.g., a transparent and scratch resistant material, such as a glass material that is commercially available under the trademark Corning® Gorilla® Glass) seals the camera aperture to cover and protect the camera 20 as well as other components located within the device housing. The camera 20 includes suitable autofocusing features to ensure quality and clarity of digital images captured by the camera. The camera 20 is connected with a nystagmus analyzer 50 (described in further detail herein) that includes a digital video recorder (DVR) 58, where the DVR 58 receives and stores digital image frames captured by the camera 20 so as to record video images (in particular, recorded video images of a portion of a subject's face including the eyes) during system operation. The camera 20 is configured with a rugged lens for outdoor field use and can also be configured with a suitable focal length that is optimized for use at testing geometries associated with field sobriety tests (e.g., as described in a conventional or other suitable field sobriety testing manual). In addition, the front side 6 of the housing includes a sensor/receiver 22, described in more detail herein, where the sensor/receiver 22 is configured to detect distances between the device 4 and a subject's face and/or wirelessly communicate with a stylus 40 associated with the device 4.

The rear side 8 of the device housing includes a display screen 24, such as an LCD (liquid crystal display), to display (e.g., replay) images recorded by the DVR of the device 4 as well as other images (e.g., selection menus, icons, etc.) associated with system operation. One or more control buttons 26 are also provided on the rear side 8 to control features of the device 4 (e.g., to control navigation between different icons and/or selection menus, to control operation of the DVR and camera 20, etc.) during system operation. While FIG. 2 depicts two input or control buttons 26, it is noted that the device 2 can include any suitable number of control buttons (e.g., more or less than two, a keypad and/or any other types of input/control buttons). Alternatively, or in addition to the control buttons, the device 2 can further include any other control features (e.g., a pressure sensitive or touch pad to facilitate "point and click" functions for a movable arrow or other icons displayed by the display screen 24, the display screen 24 can be configured as a pressure sensitive or touch screen to facilitate selections of system functions by touching and/or dragging icons or other images on the display screen 24, etc.) to facilitate system operation. In addition, the device 4 can include an audio speaker to emit one or more different types of audio signals (e.g., in combination with different video prompts on display 24) during system operation.

The upper edge portion 10 includes a power (on/off) button 28 to selectively activate or deactivate the system 2. At least one light source 30, such as an LED (light emitting diode), is provided on the upper edge portion 10 (generally depicted as two LED lights). The light source is selectively activated to aid or enhance ambient lighting conditions so as to ensure adequate video images are captured by the camera 20 during system operation (e.g., in dark, night time environments).

The device housing further includes a holding cavity or stylus port 32 at the upper edge portion 10 configured to receive and retain a stimuli stylus 40 for use with the device 2. The stylus port 32 is further configured to serve as a charging port for the stylus 40 as described further herein.

The side edge portion 12 of the device housing includes an electrical connection port 34, such as a micro-USB (universal serial bus) port, configured to connect with a suitable connector in order to facilitate transfer of data between the device 4 and another electronic device (e.g., a laptop or other suitable computer) as well as to provide a power source and/or charging of an internal battery for the device 4.

Figure 3:
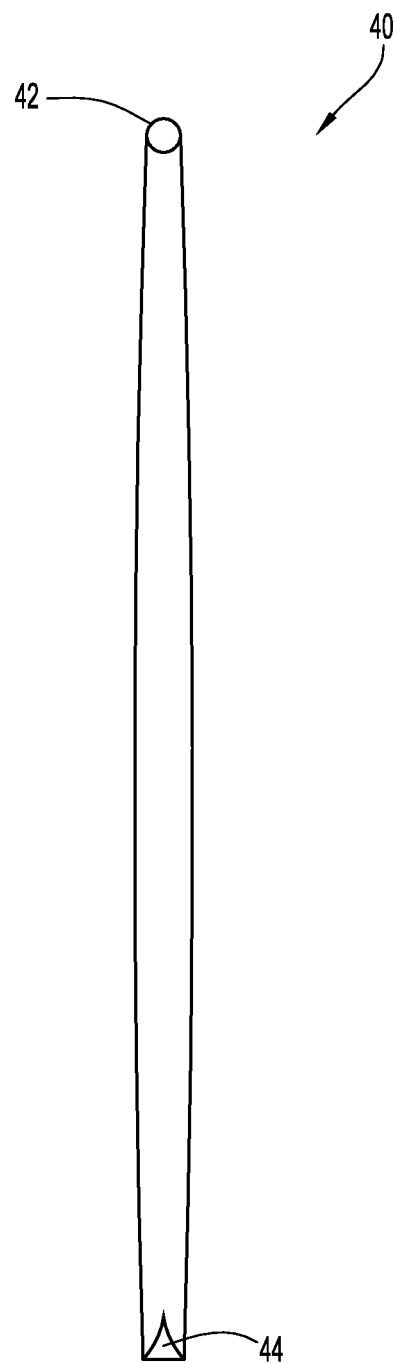
FIG. 3 is a view in elevation of a test stylus for the nystagmus testing system of FIG. 1.

Referring to FIG. 3, an elongated stylus 40 includes an embedded light 42, such as an LED light, at one end and a suitable battery 44 at its other end that is rechargeable when the stylus 40 is stored within the holding cavity 32 of the device 4. As described in further detail herein, the stylus 40 provides an indication of distance between the device 4 and the face of a test subject as well as a mechanism for directing movement of the test subject's eyes in a back-and-forth and/or up-and-down manner during HGN/VGN testing utilizing the system 2.

Figure 4:
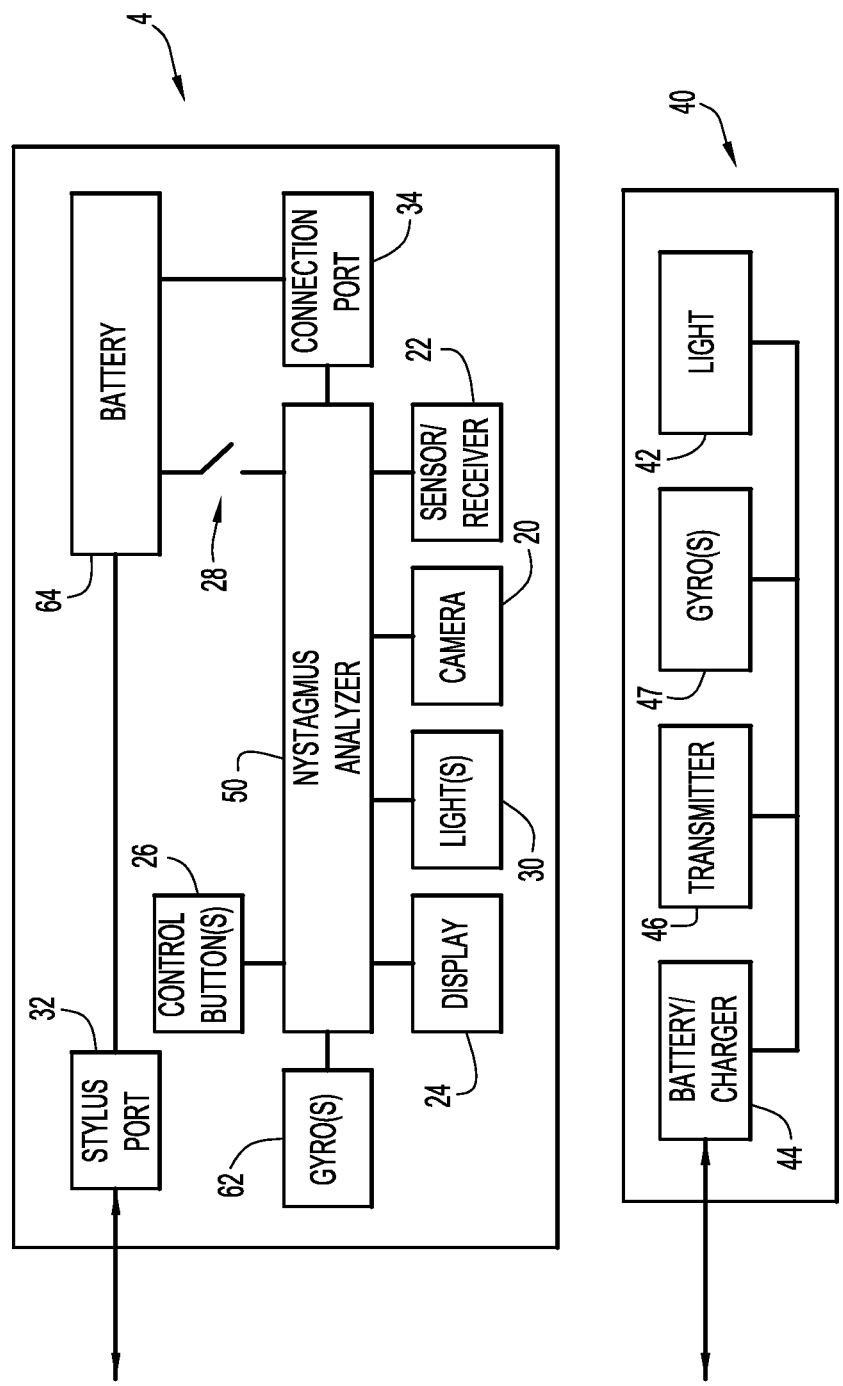
FIG. 4 is a schematic block diagram showing the components of the nystagmus testing system of FIG. 1.

Additional features of the device 4 and the stylus 40 are described with reference to the schematic block diagram of FIG. 4. In particular, the device 4 further includes a battery 64 that is connected with the stylus port 32, connection port 34 and a nystagmus analyzer 50 (via switch 28). The battery 64 can be a rechargeable battery of any suitable type (e.g., nickel cadmium, nickel metal hydride, lithium, lithium ion, etc.), where the battery 64 can be recharged by connecting to a suitable power source via the connection port 34. The battery 64 further provides power to the stylus port 32 (for charging a battery within the stylus 40) and to the nystagmus analyzer 50 to facilitate system operation. The nystagmus analyzer 50 is also connected with the connection port 34 to facilitate communication and exchange of data with other devices connected to the device 4 also via the connection port 34. In addition, the nystagmus analyzer 50 can also receive power from an alternative power supply source connected with the connection port 34.

The analyzer 50 is coupled with the control button(s) 26 to receive input information from the test administrator or user of the device 4 during system operation. The analyzer 50 is further coupled with (i.e., to control operations of) the camera 20, the sensor/receiver 22, the display 24, the light source 30, and one or more gyroscope sensors 62 disposed internally within the device housing. The one or more gyroscope sensors 62 can be of any suitable type(s) that detect motion changes (e.g., tilting, camera jitter and/or other spatial displacements) of the device 4 in one or more spatial dimensions (e.g., changes in any one or more of X, Y and Z spatial dimensions of the device 4 from an original/initialization position to a changed position based upon a three dimensional Cartesian coordinate system) and provide such detection information to the analyzer 50 to provide an indication of any change or displacement in spatial location of the device 4 (e.g., horizontal and/or vertical) in relation to an original or starting position during system operation. The analyzer 50 automatically activates the light source 30 during system operation, based upon detected ambient light conditions and/or detected images received from the camera 20, when captured camera images are detected by the analyzer as being too dark or shadowed (e.g., when subject eye movement cannot be adequately detected based upon the captured camera images being too dark).

The camera 20 can be configured to capture digital images (e.g., of the subject's face, including the subject's eyes, when the device 4 is adequately aligned with the subject's face) at any suitable frame per second (FPS) rate (e.g., at about 30 FPS or greater) and provide such images to the digital video recorder (DVR) of the analyzer 50 for storage when activated by the analyzer 50 during system operation. The sensor/receiver 22 communicates with a transmitter 46 of the stylus 40 to determine a distance between the stylus 40 and the device 4 as well as a distance between the device 4 and the test subject's face during system operation. The sensor/receiver 22 is operated by the analyzer 50 and further provides the distance information as well as other data transmitted by the stylus 40 to the device 4 during system operation.

Figure 5:
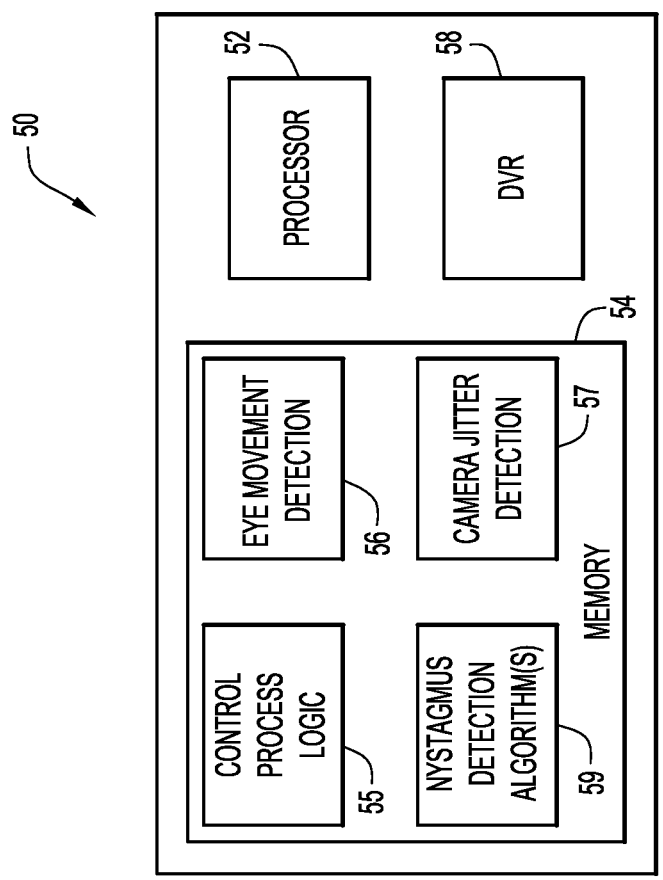
FIG. 5 is a schematic block diagram showing components of the nystagmus analyzer for the testing system of FIG. 1.

Referring to the schematic block diagram of FIG. 5, the nystagmus analyzer 50 comprises a processor 52, memory 54 and a digital video recorder (DVR) 58. The processor 52 is a microprocessor or microcontroller that executes control process logic instructions 55 (e.g., operational instructions and/or downloadable or other software applications stored in memory 54) to control operations of the device 4 during system operation. The DVR 58 includes a suitable memory module to receive and store digital images captured by the camera 20 during system operation, where the digital images are retrievable by the processor 52 for analysis of the images utilizing eye movement detection software stored by memory 54. The memory storage of the DVR 58 as well as memory 54 can include random access memory (RAM) or a combination of RAM and read only memory (ROM), magnetic disk storage media devices, optical storage media devices, flash memory devices, electrical, optical, or other physical/tangible memory storage devices.

Figure 6:
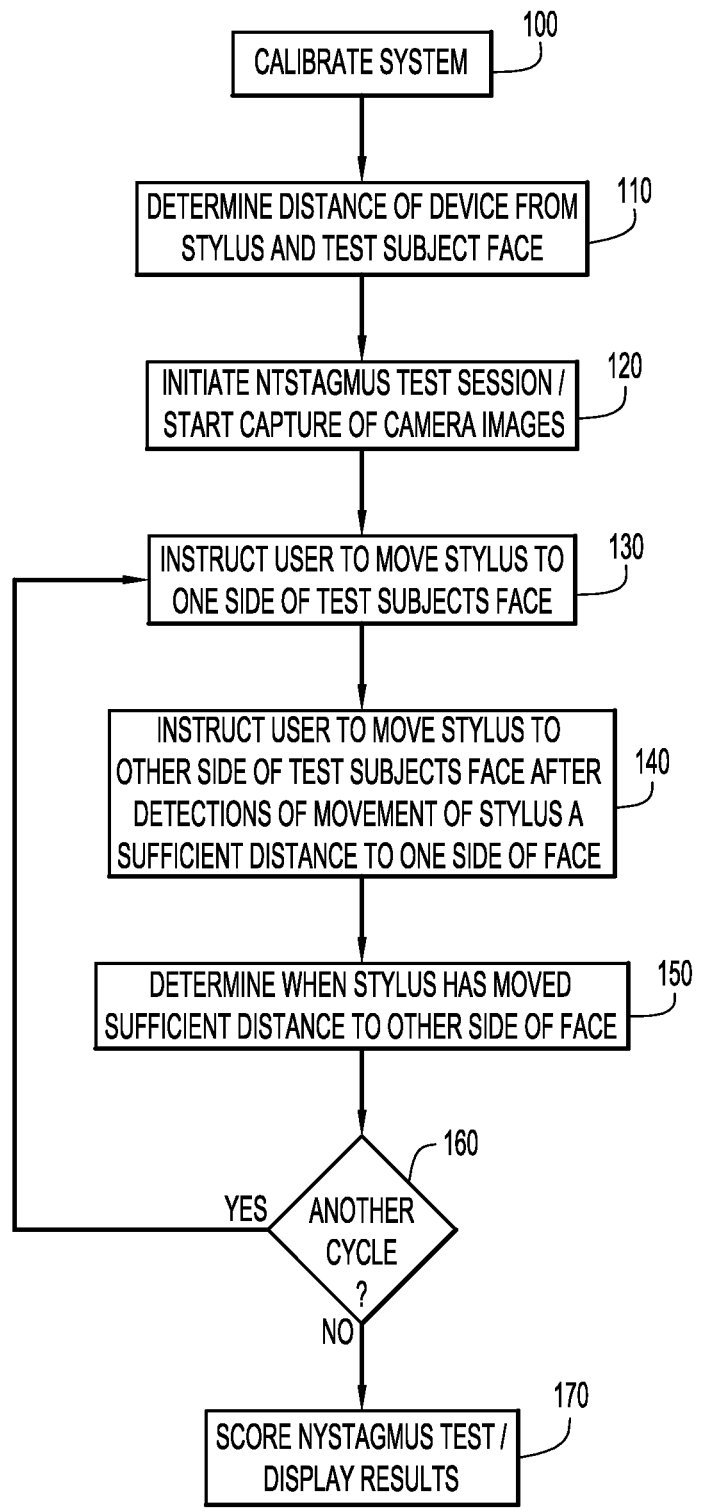
FIG. 6 is a flow chart that depicts an example process for operation of the system of FIG. 1 to perform nystagmus testing techniques as described herein.

The processor 52 executes the control process logic instructions 55 stored in memory 54 for controlling the device 4, including the performance of operations as set forth in the flowchart of FIG. 6. In general, the memory 54 may comprise one or more computer readable storage media (e.g., a memory device) encoded with software comprising computer executable instructions and when the software is executed (by the processor 52) it is operable to perform the operations described herein in connection with control process logic instructions 55. In addition, memory 54 includes eye movement detection software 56, camera jitter detection software 57, and one or more nystagmus detection algorithms 59 that are capable of detection of HGN and/or VGN based upon eye movement detection by the eye movement detection software 56.

The camera jitter detection software 57 can be of any one or more conventional or other suitable types that utilize measured movements of the device 4 as detected by the gyroscope sensor(s) 62 to determine any jitter of the camera by the test administrator/holder of the device 4 and to compensate for such camera jitter for detection of eye movements of the test subject during system operation (e.g., by adjusting for camera jitter in a horizontal or vertical direction when determining an eye movement in such direction). Some non-limiting examples of camera jitter detection and correction software and/or algorithm techniques that can be incorporated for use with the system include Vidhance® (Imint Image Intelligence), RoboRealm™ with Stabilization Plug-In (RoboRealm), Acadia II® System-On-A-Chip (Sarnoff Corporation), and a Digital Video Stabilization and Rolling Shutter Correction Using Gyroscopes (Stanford Tech Report CTSR 2011-03).

In an example embodiment, when testing for HGN in a subject, any determined jitter movement in a horizontal direction of the device 4 by the camera jitter detection software 57 (based upon measured data provided by the gyroscope sensor(s) 62) can be added or subtracted as an offset to a detected eye movement of the test subject in the horizontal direction (where the offset is added to the detected eye movement when the horizontal camera jitter is determined to be in a direction that opposes the horizontal direction of the eye movement, and the offset is subtracted from the detected eye movement when the horizontal camera jitter is determined to be in the same direction as the horizontal direction of the eye movement). A similar type of offset can be applied camera jitter in a vertical direction for VGN testing of eye movements of a test subject.

The eye movement detection software 56 can be of any one or more conventional or other suitable types that analyze recorded camera images stored by the DVR 58 and, based upon the analysis of such recorded images, detect and identify one or both eyes on a face within each camera image and further detect and track eye movements based upon a series of sequential digital image frames including the eyes. Some non-limiting examples of eye movement detection software that can be implemented for use with the system include Eye Tracking Software Nyan 2.0XT (Interactive Minds), S2 Eye Tracker API (Miramatrix Inc.), and ITU Gaze Tracker (ITU Gaze Group).

In an example embodiment, the eye movement detection software 56 can identify and locate the iris of one or each of the eyes of the test subject in each captured image frame in which the test subject's face is present, and the eye movements can be tracked based upon a changing location and positioning of the iris for one or both eyes in relation to an initial/starting position as determined at an initial/starting frame and/or in relation to a position determined for any other preceding frame for a series of sequential captured image frames (e.g., a series of sequential image frames that are captured during a nystagmus testing session utilizing the camera 20). Based upon such eye movement detection, the software 56 can be configured to develop an eye tracking or eye movement trajectory plot or map that indicates whether there is any sudden lateral/horizontal and/or vertical jerking movements of the subject's eyes during a test session. For example, trajectory vectors for each eye can be determined on a frame-by-frame basis in the series of sequential captured image frames being analyzed utilizing the software 56, and such trajectory vectors can be combined to generate an eye movement trajectory plot or map. The eye movement/trajectory plot can be displayed, for example, utilizing the display 24 of the device 4.

The nystagmus detection algorithm(s) software 59 comprises one or more algorithms which determine a degree of lateral/horizontal and/or vertical jerking movement that occurs, based upon the image frames that have been captured by the camera 20 and stored in the DVR 58 during a test session and based upon the eye movement detections of such captured image frames as determined by software 56. The algorithms of software 59 can apply any one or more suitable and recognized standards for an indication of nystagmus based upon the degree of horizontal and/or vertical jerking of the eyes during eye movements by a test subject to the left and the right (e.g., to a location of about 45° to the left or the right from a central location between the test subject's eyes). For example, the algorithm(s) may apply one or more standards for a particular legal jurisdiction which define a particular nystagmus test and measured degree of jerking eye movement that adequately establish intoxication or other impairment of a test subject during a field sobriety test utilizing the system 2.

Referring again to FIG. 4, the stylus 40 includes a light source 42, a battery 44, a transmitter 46, and one or more gyroscope sensors 47. The battery 44 is rechargeable and can be of any suitable type (e.g., nickel cadmium, nickel metal hydride, lithium, lithium ion, etc.) to provide power to the light source 42 and transmitter 46 of the stylus 40. The battery 44 is charged by the stylus port 32 of the device 4 when the stylus 40 is inserted at the battery side end within the port 32 (where battery 64 and/or another power source connected with connection port 34 provide power to recharge battery 44).

The transmitter 46 of the stylus provides data signals to the sensor/receiver 22 of the device 4, where such data signals are then communicated to the processor 52 of the analyzer 50 for use during system operation. The transmitter 46 and sensor/receiver 22 can exchange data signals in any suitable wireless manner, such as by an infrared (IR) signal reception/transmission, radio frequency (RF) signal reception/transmission, etc. The transmitter is coupled with one or more gyroscope sensors 47, where the gyroscope sensor(s) 47 can be of the same or similar types as the sensor(s) 62 for device 4 in order to detect a positioning of the stylus 40 in one or more dimensions in relation to the device 4. For example, the gyroscope sensor(s) 47 can be configured within the stylus 40 to provide an indication of the orientation of the stylus 40 with respect to a supporting surface (e.g., a ground surface) upon which the test administrator/holder of the stylus 40 is supported. In addition, the gyroscope sensor(s) 47 and/or transmitter 46 can provide an indication of an orientation of the stylus 40 with respect to the device 4 and/or the test subject's face, e.g., in order to determine whether the stylus has been moved to a sufficient offset angle from a central portion of the subject's face (e.g., to determine whether the stylus 40 has been moved to about 45° to the left or right of a central portion between the eyes of the test subject's face).

The light source 42 of the stylus 40 can be activated in a number of different ways. In one example, the light source 42 can be activated whenever the stylus 40 is disengaged from the stylus port 32 of the device 4. In another example, the stylus 40 can include an activation button or switch to allow the test administrator to selectively activate (i.e., turn on or off) the light source 42 during system operation.

While the example embodiment shows the stylus 40 and device 4 as separate elements that wirelessly couple with each other to exchange data signals during system operation, it is noted that, in an alternative embodiment, the stylus can instead be hard wire connected with the hand-held device. In such an embodiment, the stylus would not require a separate rechargeable battery or a wireless transmitter but instead would receive power and convey data to the processor of the device via the hard wire connection.

Example embodiments of system operation are now described with reference to the device depicted in FIGS. 1-5 and 7 and also the block diagram depicted in FIG. 6. It is noted that, during system operation, the test administrator can hold the device 4 in one hand (e.g., the test administrator's left hand) while holding the stylus 40 in the other hand (e.g., the test administrator's right hand), where operation of input/control buttons 26 and/or other system features of the handheld device 4 can be controlled by the test administrator's one hand while the test administrator's other hand operates the stylus 40.

Upon powering up the device 4 (via power button 28), the system 2 undergoes a calibration prior to engaging in a nystagmus test session (step 100). In this calibration process, the processor 52 prompts the test administrator of the device (e.g., a police officer or other person trained to use the device) to align the camera 20 such that clear images of the test subject's face 70 can be captured and recorded by the DVR 58. This prompt, as well as all other prompts during system operation, can be displayed by the display 24. In addition, one or more different types of audio signals can also be utilized by the system 2 (e.g., in combination with video displays) to notify a test administrator about issues or system requirements during system operation.

The system 2, via processor 52 and the control process logic 55, controls the camera 20 to automatically adjust focus on the test subject's face 70, as necessary, so as to ensure that clear, focused images of the test subject's eyes can be recorded. For example, the eye movement detection software 56 can be utilized to identify whether portions of one or both eyes (e.g., the iris) are detectable from the images captured by the camera 20 during calibration. In the event a clear image of the test subject's eyes cannot be determined, the system 2 instructs the test administrator (via prompts on the display 24 and/or via audio signals) to move the device 2 closer or further away from the test subject's face 70 and/or to properly align the device 2 with the face 70 (in the event the test subject's eyes are not within the camera's view). The display 24 can also display the captured images of the face 70 during calibration to provide the test administrator with feedback and guidance regarding how well focused the captured images are based upon positioning of the device 2 relative to the test subject's face 70. In addition, the system 2 can determine whether ambient light conditions require activation of the light source(s) 30. For example, in a dark (night time) or heavily shaded environment, the images captured by the camera 20 may be too dark to provide enough contrast to adequately identify or detect eye movements. In such a scenario, the system 2 automatically activates and/or adjusts the intensity of the light source(s) 30 to ensure adequate contrast of the test subject's face 70 in order to allow for adequate focusing of the camera 20 and capturing of clear images of the test subject's face 70.

In addition to focusing the camera 20 during calibration, the system 2 can further determine an approximate distance of the device 2 from the stylus 40 and/or the test subject's face 70 (step 110). This is achieved by the system 2 instructing the test administrator to move the stylus 40 (which has been withdrawn from the stylus port 32) from the device 2 to an approximated distance from the test subject's face 70 such that it is between the device 2 and the test subject's face 70. For example, the system 2 can instruct the test administrator, via a prompt on the display 24, to move the stylus 40 from the device 2 to a distance of approximately 12 inches (about 30.5 cm) to 18 inches (about 45.7 cm) from the test subject's face 70. The test administrator may further be prompted to tap an end of the stylus 40 (e.g., the end including the light source(s) 42) to the sensor/receiver 22 of the device 4, and then move the stylus away from the device 4 to its approximate position from the test subject's face 70. The tapping of the stylus 40 to the sensor/receiver 22 can be performed to initiate a communication between the transmitter 46 of the stylus 40 and the sensor/receiver such that signals sent from the transmitter 46 provide a distance indication to the device 4 regarding the distance of the stylus 40 from the device 4. The distance of the device 4 from the test subject's face 70 can then be determined based upon the determined distance between device 4 and stylus 40 and the approximated distance the test administrator holds the stylus 40 from the test subject's face 70.

The system 2 further instructs the test administrator during this distance determination step (step 110) to position the stylus 40 at approximately a center point of the test subject's face 70 (e.g., between the test subject's eyes) so as to establish an initial or starting point for the stylus 40 prior to beginning a test sequence. The test administrator can press one of the input/control buttons 26 to indicate when the stylus 40 is in its initial/starting position, and the gyroscope sensor(s) 62, 47 of both the device 4 and the stylus 40 can be initialized (i.e., calibrated to values that are assigned initial or starting positions) at these relative positions of the device 4 and stylus 40, where these initial relative positions provide the basis or starting point for determining camera jitter or other movements of the device 4 and deliberate movements of the stylus 40 to the left and right of the test subject's eyes during nystagmus testing.

After suitable calibration has been achieved and approximate distances between the device 4 and the stylus 40 and also the test subject's face 70 have been determined, where it has further been determined that adequately focused images with appropriate contrast can be captured of the test subject's face 70 so as to accurately determine eye movements, the system 2 prompts the test administrator (via the display 24 and/or via an audio signal) to initiate a nystagmus test session (step 120). The test administrator notifies the system 2 that the test is being initiated, e.g., by pressing one of the input/control buttons 26. This initiates capturing of images of the test subject's face 70 by the camera 20 at a suitable FPS rate, where the digital images are stored as a video stream of consecutive image frames by the DVR 58 of the analyzer 50.

The system can be configured to conduct the nystagmus test according to any particular protocols and/or procedures that are known for indicating impairment. In particular, the National Highway Traffic and Safety Administration (NHTSA) has developed an HGN testing guide for field use by a test administrator (e.g., a police officer). The NHTSA HGN testing guide indicates that the test administrator should look for six clues (three in each eye) during testing of the test subject that would indicate impairment. The left eye can be checked first, followed by the right eye. The tests are set forth as follows:

1. Lack of smooth pursuit—the test administrator moves an object slowly but steadily from the center of the subject's face toward the left ear. The left eye should smoothly follow the object, but if the eye exhibits nystagmus, the test administrator notes the clue. The test administrator then checks the right eye in the same manner (by moving the object slowly and steadily from the center of the subject's face toward the right ear).

2. Distinct nystagmus at maximum deviation—starting again from the center of the suspect's face, the test administrator moves the object toward the left ear, bringing the eye as far over as possible, and holds the object there for a short period of time (e.g., about four seconds). The test administrator notes the clue if there is a distinct and sustained nystagmus at this point. The test administrator holds the object at maximum deviation for this period of time (e.g. at least about four seconds) to ensure that quick movement of the object did not possibly cause the nystagmus. The test administrator then checks the right eye in the same manner. This is also referred to as "end-point" nystagmus.

3. Angle of onset of nystagmus prior to 45°—the test administrator moves the object at a speed that would take about four seconds for the object to reach the edge of the suspect's left shoulder. The test administrator notes this clue if the point or angle at which the eye begins to display nystagmus is before the object reaches 45° from the center of the suspect's face. The test administrator then moves the object toward the suspect's right shoulder. Generally, 45° from center on either left or right side of the test subject is at the point where the object is in front of the tip of the subject's left or right shoulder.

The control process logic 55 of the system 2 can be configured to instruct the test administrator to perform the operations in accordance with NHTSA HGN nystagmus testing guidelines (as set forth above) and/or in accordance with any other desired testing protocols or procedures during a nystagmus test session.

In accordance with the protocols/guidelines for nystagmus testing that are to be used during a test session (as stored by memory 54, e.g., as part of the control process logic 55 and/or any other suitable instructional software to be used by the processor 52), the system 2 prompts (e.g., via the display 24 and/or via an audio signal) the test administrator to move the stylus 40 in a direction toward one side of the test subject's face 70 (step 130), such as toward the right side (from the test administrator's perspective) of the test subject's face 70. The stylus 40 periodically transmits signals via its transmitter 46 to the sensor/receiver 22 of the device, including measured data from the gyroscope sensor(s) 47, which provides an indication of the change in position of the stylus 40 relative to the device 4. The system can further instruct the test administrator to move the stylus 40 at a particular speed (e.g., to move the stylus such that it takes about 4 seconds to reach the one side of the subject's face 70, at or near the subject's ear and/or shoulder) while monitoring the speed of movement of the stylus 40 via the communication between the stylus transmitter 46 and the device sensor/receiver 22.

The position information provided to the device 4 by the stylus 40 provides an indication of how far the stylus 40 has moved from its central position relative to the test subject's face 70 (i.e., between the test subject's eyes). The system 2 determines when the stylus 40 has moved a sufficient distance to one side of the test subject's face 70 (e.g., approximately 45°, so as to be at or near the test subject's corresponding ear and/or shoulder) so as to facilitate sufficient capture of eye movements of the test subject in one direction due to the test subject focusing his/her gaze upon the stylus 40. When it has been determined that the stylus 40 has been moved to its furthest point to the one side of the face 70, the system 2 can optionally prompt the test administrator to hold the stylus 40 at this location for a period of time (e.g., about 4 seconds) while the camera 20 continues to capture digital images to be stored by the DVR 58.

After the stylus 40 has been maintained at the one side of the test subject's face 70 for a sufficient period of time to facilitate capture of digital images of the face 70 (including eye movements), the system 2 prompts the test administrator (via the display 24 and/or an audio signal) to move the stylus 40 in the other/opposing direction relative to the test subject's face 70 (step 140). When the system 2 has determined that the stylus 40 has moved a sufficient distance in the other direction from its original or starting position (e.g., a determination that the stylus 40 has moved in the other direction about 45° from its original or starting position relative to a central location relative to the test subject's face 70, which is at a location at or near the test subject's ear and/or shoulder), the system 2 prompts the test administrator to cease moving the stylus 40 in the opposing direction (step 150). The camera continues to capture images of the test subject's face 70 during the movements of the stylus 40 in each direction.

Figure 7:
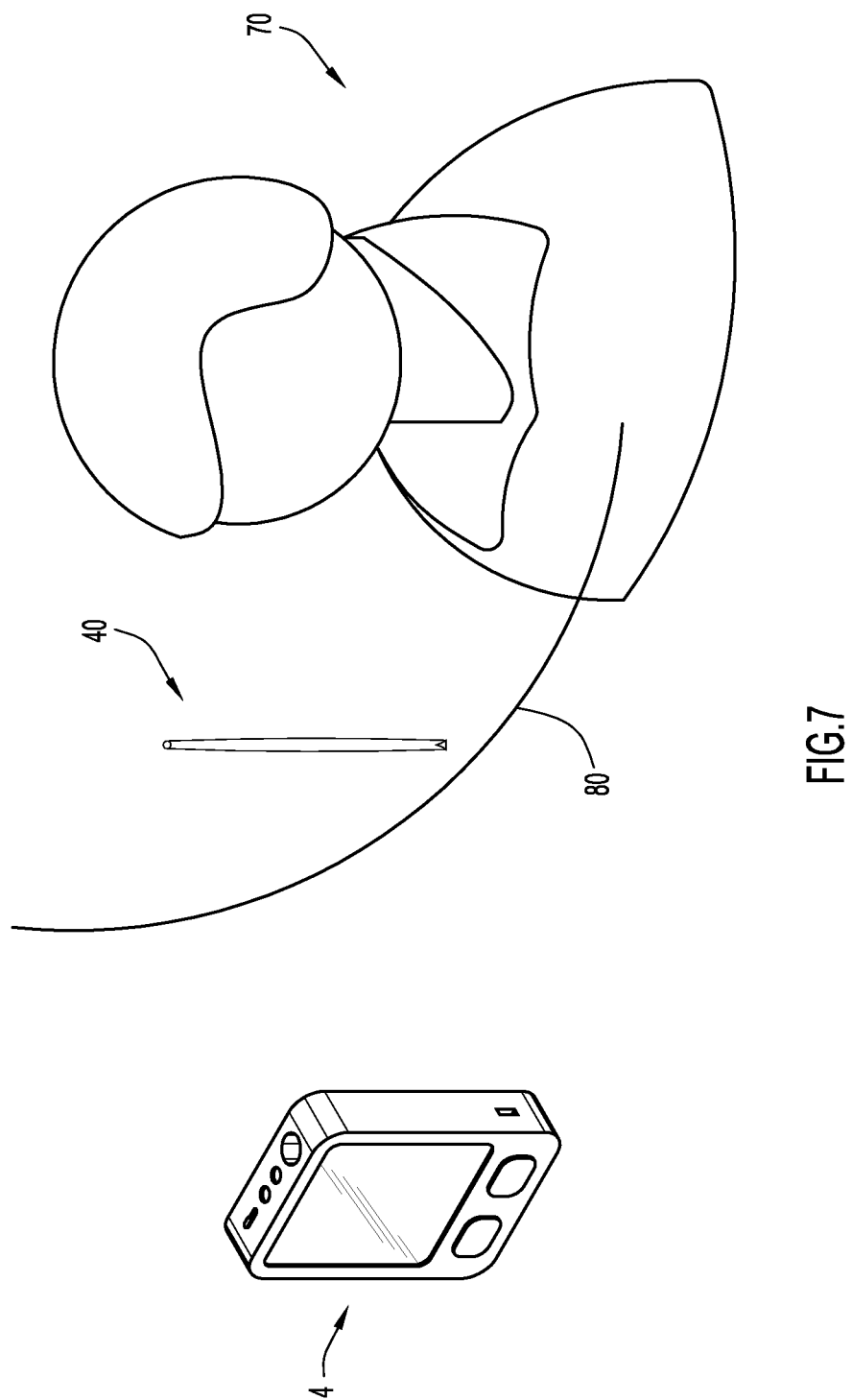
FIG. 7 is a schematic view demonstrating operation of the system of FIG. 1 for testing nystagmus of a subject.

The arc 80 depicted in FIG. 7 shows the general or approximate path or trajectory in which the stylus 40 travels in one direction (e.g., approximately 45° to the right of the center of the test subject's face 70) and then in the opposite direction (e.g., approximately 45° to the left of the center of the face 70) during the test session. After movement of the stylus 40 by the test administrator a single time in both directions, generally along the arc path 80, a single cycle of the nystagmus test session has occurred. The test subject has been advised by the test administrator to keep the face 70 aligned in the same direction (generally straight ahead and pointed toward the device 4) while moving the test subject's eyes in a direction following the path of movement of the stylus 40 (e.g., keeping the test subject's eyes focused on the light source 42 at the tip of the stylus 40 while the stylus 40 is moving).

The system 2 can decide how many times the test administrator must move the stylus 40 to each side of the test subject's face 70 (step 160). The number of times or cycles at which the test administrator must move the stylus in opposing directions relative to the test subject's face 70 (e.g., one complete cycle, or two or more complete cycles) may be based upon a particular nystagmus test being implemented (e.g., based upon the requirements for one or more nystagmus detection algorithms 59 being implemented to analyze the eye movement detection results), by a predetermined number of cycles established during calibration (e.g., the number of cycles might be input to the device 4 by the test administrator prior to a test sequence being implemented), etc. For example, when conducting a test in accordance with the NHTSA HGN nystagmus test guidelines, the test session may employ at last 2 and possibly more cycles. Upon completing the last cycle, the system instructs the test administrator that the test session is complete, where the test administrator can then stop moving the stylus 40 relative to the test subject. The system 2, via the analyzer 50, also determines a score for the test session (step 170), where an indication of the score can be displayed by the display 24.

The determination of a score for the test session (step 170) first involves an analysis of the series of images captured by the camera 20 and stored within the DVR 58 of the nystagmus analyzer 50 to detect and track eye movements. As previously noted, the camera 20 continues to capture images of the test subject's face 70 (e.g., at a rate of about 30 FPS or greater) during the test session while the test administrator moves the stylus 40 to each side of the face 70. The processor 52 utilizes the eye movement detection software 56 as well as camera jitter detection software 57 (which determines camera jitter based upon factors including spatial displacement information of the device 4 as determined via gyroscope sensor(s) 62) to obtain information regarding movement of the test subject's eyes (where the eye movement detection software 56 identifies, e.g., the iris of one or both of the test subject's eyes in each captured image frame). As previously noted, any camera jitter detected by the analyzer 50 in the same spatial dimension(s) as the those in which eye movements are being monitored by the system 2 (e.g., horizontal and/or vertical eye movements) can accordingly be applied as a plus (+) or minus (−) offset to the eye movement detection so as to negate or remove the effects of the camera jitter. Thus, the camera jitter detection processing ensures that the movements detected in a series of captured image frames is only the result of eye movements and not due to camera jitter movements.

The subject's eye movement is in essence tracked by the analyzer 50 in correspondence with movement of the stylus 40, where the positioning of the stylus 40 relative to the device 4 is determined at all times during the test session based upon the initial calibration (in which the original positions of the device 4 and stylus 40 relative to each other and the test subject's face 70 are determined) and the measurements by the gyroscope sensor(s) 47 and/or other signals provided by the transmitter 46 of the stylus 40 to the sensor/receiver 22 of the device 4. The eye movement detection software 56 can be configured to generate frame-to-frame motion vectors for each eye as well as an overall eye movement tracking or motion map for each eye.

The detection and tracking of eye movements during the test session by the analyzer 50 (utilizing the eye movement detection software 56) can occur on a frame-by-frame basis during the test session (i.e., while images are being captured by the camera 20). Alternatively, the video frames captured by the camera 30 and stored by the DVR 58 can be analyzed by the analyzer 50 on a frame-by-frame basis after termination of a test session to detect and track eye movements of the test subject.

The processor 52 utilizes the nystagmus detection algorithm software 59 to make a determination regarding whether the eye movement detection and tracking indicates a presentation of nystagmus or a presentation of a degree of nystagmus approaching or exceeding a threshold which correlates with impairment of the test subject (e.g., impairment due to the effects of alcohol consumed by the test subject, such as a blood alcohol concentration or BAC level of the subject that exceeds a threshold value, and/or any other form of impairment that can be detected by the presentation of nystagmus by the test subject during the test session). For example, the eye movement detection and tracking information (e.g., presented in the form of a motion map for each eye and/or in any other suitable manner) can reveal lateral/horizontal and/or vertical "jerking" of the eyes that occurred during the test session, and the degree to which such "jerking" has occurred can be analyzed by the software 59 to correlate this with whether nystagmus has occurred and/or to what degree nystagmus has occurred. Certain legal jurisdictions may have different standards for which types or what degrees of eye "jerking" and/or other eye movements sufficiently constitute nystagmus at a level that indicates impairment of the test subject (e.g., an indication that the test subject is impaired by the effects of alcohol). The nystagmus detection algorithm software 59 that is implemented by the analyzer 50 is configured to utilize standards for assessing nystagmus caused by eye movements based upon the legal jurisdiction within which the system 2 is being used.

After analysis of the detected/tracked eye movements utilizing the nystagmus detection algorithm software 59, a determination is made regarding whether or to what degree the test subject may be exhibiting some form of impairment. The determination can be determined as a score value (e.g., indicating probability or likelihood of a certain level of impairment of the test subject), or simply as a PASS or FAIL value (where PASS indicates the test subject is not considered legally impaired, while a FAIL value indicates the test subject is considered legally impaired). For example, in a legal jurisdiction in which a BAC of 0.08 or greater is considered legally intoxicated (where such BAC level, e.g., prohibits the legally intoxicated individual from operating motorized vehicles or other equipment), a correlation by the analyzer 50 of a detected eye movement with a BAC value that meets or exceed 0.08 would result in a high probability score of legal intoxication or a FAIL indication. The determined score or PASS/FAIL indication is displayed on the display 24 of the device 4 (and/or a corresponding audio signal can be provided by the device 4).

The analyzer 50 can further store in the DVR 58 the captured camera images obtained from the test session as well as all information/data obtained or derived from the test session within memory 54. In addition, the analyzer 50 can be configured to conduct and score multiple test sessions. Captured images and associated data from test sessions can be transferred from the device 4 to other devices (e.g., computer databases, laptops, etc.) via the connection port 34.

The system 2 can further be configured to utilize the interface between the system 2 and the administrator (e.g., display 24, input buttons 26 and/or any other communication features of the device 4) so as to provide additional features for the system 2. For example, the captured digital image frames stored by the DVR 58 can be replayed as a video clip on display 24 based upon an input prompt by the administrator. As previously noted, the system 2 can display any suitable icons, menus, etc. to facilitate interaction with the administrator to perform replay functions as well as other functions (e.g., the administrator can access information from one or multiple test sessions saved in memory 54 and DVR 58 to replay video clips of any of the saved sessions or further analyze any of the saved test sessions utilizing the software stored in memory 54).

Thus, the nystagmus test system and corresponding methods facilitate easy and reliable testing of nystagmus of a test subject in the field by an administrator, where the system automatically determines the occurrence of nystagmus after administration of the test and provides an indication of such determination soon after the test has been administered.

In an optional alternative embodiment, the system may include a device such as the device 4 described above but with no corresponding stylus that is wirelessly linked with the device. In such an embodiment, the test administrator can still use a stylus or other device (e.g., a pen) that is not wirelessly linked with the hand-held device but provides the stimuli for directing movement of the test subject's eyes during a test session. The system still captures image frames of the test subject's face and detects/tracks eye movements that are used to determine a possible occurrence and/or degree of nystagmus of the test subject.

Other modifications to the system described above are also possible (e.g., utilizing a hard wired instead of a wireless stylus, providing an audio speaker for the device to provide different audio signals during system operation, etc.). In addition, the system can be configured to load nystagmus detection algorithm software and/or other types of software (e.g., upgraded software or different types of software corresponding to a particular legal jurisdiction in which the system is to be used) from a source (and via the connection port of the device) into the memory of the nystagmus analyzer. The system can further be configured to test for indication of other forms of impairment due to the presentation of eye nystagmus during a test session, such as impairments due to certain types of controlled substances (e.g., narcotics, stimulants, other forms of synthetic and/or pharmaceutical drugs, etc.).

Having described example embodiments of systems for automated detection of eye nystagmus and corresponding methods associated with such systems, variations and changes will be suggested to those skilled in the art in view of the teachings set forth herein. It is therefore to be understood that all such variations, modifications and changes are believed to fall within the scope of the present invention as defined by the appended claims.

What is claimed:

1. A system for detection of eye nystagmus in a test subject, the system comprising:
   a camera to capture digital images in a series of sequential digital image frames of the test subject's face when the camera is located a selected distance from the test subject;
   a sensor to determine a distance between the camera and the test subject's face; and
   an analyzer comprising:
      a memory configured to store data; and
      a processor configured with logic to:
         detect and track eye movements of the test subject based upon an analysis of digital image frames captured by the camera, wherein eye movements are tracked via analysis of a plurality of the captured digital image frames on a sequential frame-by-frame basis; and
         based upon the eye movement detection and tracking, provide an indication regarding whether the test subject exhibits nystagmus;
         wherein the system is configured for operation while being separated one or more distances from the test subject's face such that no portion of the system engages with the test subject's face.

2. The system of claim 1, further comprising:
   a portable device that houses the camera and the analyzer; and
   a stylus in communication with the analyzer to facilitate a determination by the analyzer of a position of the stylus relative to the device when the stylus is moved to different locations relative to the test subject's face.

3. The system of claim 2, wherein the stylus includes a transmitter and the portable device includes a receiver to receive signals from the stylus such that the communication between the stylus and the portable device is a wireless communication.

4. The system of claim 3, wherein the portable device includes a port configured to receive at least a portion of the stylus.

5. The system of claim 4, wherein the stylus includes a rechargeable battery that is charged by the portable device when the portion of the stylus is received within the port.

6. The system of claim 2, wherein the stylus includes a light at an end of the stylus that is selectively activated during system operation.

7. The system of claim 2, wherein the stylus includes at least one gyroscope sensor that provides an indication of an orientation and spatial displacements of the stylus in relation to the portable device.

8. The system of claim 1, wherein the system further includes at least one gyroscope sensor that provides a measurement of spatial displacements of the camera due to jitter during system operation, wherein the processor is further configured with logic to receive spatial displacement information from the at least one gyroscope sensor and adjust tracking determinations of eye movements of the test subject based upon the spatial displacement information.

9. The system of claim 1, further comprising:
   a display to display features during system operation, wherein system operation features include providing the indication regarding whether the test subject exhibits nystagmus.

10. A computer-implemented method for detection of eye nystagmus in a test subject, comprising:
    capturing digital images in a series of sequential digital image frames of the test subject's face during a test session in which an administrator moves a stylus toward one side and another side of the test subject's face while instructing the test subject to gaze at the moving stylus;

detecting and tracking eye movements of the test subject based upon an analysis of the captured digital image frames, wherein eye movements are tracked via analysis of a plurality of the captured digital image frames on a sequential frame-by-frame basis; and based upon the eye movement detection and tracking, providing an indication regarding whether the test subject exhibits nystagmus, wherein the indication comprises an output value corresponding with a likelihood of an impairment of the test subject, the output value comprising at least one of a score, a pass value indicating the test subject is not impaired and a fail value indicating the test subject is impaired.

11. The method of claim 10, wherein the digital images are captured by a camera integrated within a portable device, the portable device further comprising a processor that performs the detecting and tracking of eye movements of the test subject and provides an indication regarding whether the test subject exhibits nystagmus.

12. The method of claim 11, further comprising:
facilitating communication between the stylus and the portable device in order to determine a position of the stylus relative to the portable device when the stylus is moved to different locations relative to the test subject's face.

13. The method of claim 12, wherein the stylus includes a battery, and the method further comprises:
charging the stylus in a port of the portable device.

14. The method of claim 12, further comprising:
activating a light at an end of the stylus during movements of the stylus in relation to the test subject's face.

15. The method of claim 11, further comprising:
measuring any one or more spatial displacements of the portable device during capturing of digital images by the camera; and adjusting tracking determinations of eye movements of the test subject based upon the measured spatial displacement information.

16. The method of claim 11, further comprising:
displaying the indication regarding whether the test subject exhibits nystagmus on a display of the portable device.

17. The method of claim 11, further comprising:
storing the captured digital images and other information associated with the tracking and detection of eye movements and the indication regarding whether the test subject exhibits nystagmus in a memory of the portable device.

18. The method of claim 17, further comprising:
connecting the portable device with another electronic device; and transferring data comprising at least one of the stored captured digital images and at least a portion of the other information from the portable device to the other electronic device.

* * * * *